US00PP10212P

United States Patent [19]

Wain

[11] Patent Number: Plant 10,212

[45] Date of Patent: Jan. 27, 1998

[54] CHRYSANTHEMUM PLANT NAMED 'BLUE JAY'

[75] Inventor: Peter Wain, VR Portsmouth, United Kingdom

[73] Assignee: Cleangro Ltd., Chichester, United Kingdom

[21] Appl. No.: 731,781

[22] Filed: Oct. 18, 1996

[51] Int. Cl.[6] ..... A01H 5/00

[52] U.S. Cl. ..... Plt./76

[58] Field of Search ..... Plt./76, 80, 81

*Primary Examiner*—Howard J. Locker
*Attorney, Agent, or Firm*—C. A. Whealy

[57] ABSTRACT

A distinct cultivar of Chrysanthemum plant named 'Blue Jay', characterized by its vigorous and upright growth habit; freely branching plant habit; decorative-type inflorescences; dark lavender ray florets; numerous inflorescences per plant; and good garden performance.

2 Drawing Sheets

The present invention relates to a new and distinct cultivar of Chrysanthemum plant, botanically known as *Dendranthema grandiflora* and referred to by the cultivar name Blue Jay.

The new cultivar is a product of a planned breeding program conducted by the inventor in Chichester, West Sussex, United Kingdom. The objective of the breeding program was to create new Chrysanthemum cultivars having desirable inflorescence colors and good garden performance.

The new cultivar originated from a cross made by the inventor of the cultivar Lynn (U.S. Plant Pat. No. 8,171) as the female, or seed, parent with the proprietary selection 10/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Blue Jay'. These characteristics in combination distinguish 'Blue Jay' as a new and distinct cultivar:

1. Vigorous and upright growth habit.
2. Freely branching plant habit.
3. Decorative-type inflorescences.
4. When opening, ray florets are dark magenta; when opened, ray florets are dark lavender.
5. Numerous inflorescences per plant.
6. Numerous ray florets per inflorescence.
7. Good garden performance.

The cultivar Blue Jay has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum are more vigorous, more upright, and flower later than plants of the female parent, the Chrysanthemum cultivar Lynn. Additionally, the ray floret color of the new Chrysanthemum is darker than the ray floret color of the cultivar Lynn. In the same comparisons, plants of the new Chrysanthemum differed from the male parent in ray floret color and inflorescence form as the selection 10/GM/94 has yellow ray florets and a daisy inflorescence form.

Plants of the new Chrysanthemum can be compared to the cultivar Debonair (U.S. Plant Pat. No. 5,324). However, in side-by-side comparisons conducted in Oxnard, Calif. under commercial practice, plants of the new Chrysanthemum differed from plants of the cultivar Debonair in the following characteristics:

1. When opening, plants of the new Chrysanthemum have darker ray floret color than plants of the cultivar Debonair.
2. Plants of the new Chrysanthemum are more vigorous and denser than plants of the cultivar Debonair.
3. Leaves of plants of the new Chrysanthemum have deeper sinuses than leaves of plants of the cultivar Debonair.
4. Plants of the new Chrysanthemum have longer peduncles than plants of the cultivar Debonair.

A detailed comparison of plants of the new Chrysanthemum and the cultivar Debonair appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical flowering 16.5-cm container of 'Blue Jay' with one cutting in the container.

The second photograph comprises a close-up view of five leaves at different stages of development, an opening inflorescence and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif. under commercial practice in a glass-covered greenhouse with average night temperatures of 18C, average day temperatures of 30C, and light levels of 2,000 (cloudy conditions) to 9,000 (sunny conditions) foot-candles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Blue Jay.

Commercial classification:
Garden chrysanthemum.

Parentage:

*Female, or seed, parent.*—*Dendranthema grandiflora* cultivar Lynn (U.S. Plant Pat. No. 8,171).

*Male or pollen, parent.*—*Dendranthema grandiflora* proprietary selection 10/GM/94.

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Vigorous, stems upright, uniform habit and freely branching.

*Plant height.*—About 22 cm.

*Lateral branch length.*—about 20 cm.

*Quantity of lateral branches after removal of apical meristem.*About 4.

*Stem color.*—146C.

*Foliage description.*—Number of leaves per plant: About 60. Number of leaves per lateral branch: About 15. Leaf arrangement: Alternate. Leaf size, fully expanded: Length: About 5 cm. Width: About 4 cm. Leaf apex: Rounded, slightly apiculate. Leaf base: Acute to attenuate. Leaf margin: Palmately lobed. Leaf texture: Abaxial and adaxial surfaces slightly pubescent, smooth and dull. Veins prominent on abaxial surface. Petiole length: About 2 cm. Color: Young foliage adaxial surface: 137C. Young foliage abaxial surface: 137D. Fully expanded foliage adaxial surface: 147A. Fully expanded foliage abaxial surface: 147B. Venation adaxial surface: 147C. Venation abaxial surface: 147B. Petiole: 147C.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plants flower in the autumn. At other times of the year, inflorescence initiation and development can be induced under short day/long night conditions (at least 13.5 hours of darkness). Plants exposed to about 4 weeks of long day/short night conditions after sticking followed by photoinductive short day/long night conditions, flower about 49 days later.

*Quantity of infloreseences.*—About 6 inflorescences per flowering stem. Diameter: About 4.3 cm. Depth (height): About 1.8 cm. Diameter of disc: About 7 mm.

*Opening inflorescences.*—Bud shape: Flattened. Bud size: Length: About 7 mm. Width: About 1 cm. Bud color: 70A.

*Ray florets.*—Shape: Spatulate. Size: Length: About 1.8 cm. Width: About 6 mm. Apex: Rounded, emarginate. Base: Acute. Margin: Entire. Texture: Satiny, smooth and glabrous. Aspect: Flat. Number of ray florets per inflorescence: About 156. Color: When opening, adaxial surface: 70B. When opening, abaxial surface: 70D. Mature, adaxial surface: 77C. Mature, abaxial surface: 75C. Fading to: 75B.

*Disc florets.*—Shape: Tubular. Size: Length: About 4 mm. Width: About 1 mm. Number of disc florets per inflorescence: About 28. Color: Immature: 6A. Mature: 6A.

*Peduncle.*—Aspect: Strong and angled about 35° to the stem. Length: First peduncle: About 3.8 cm. Fourth peduncle: About 6 cm. Texture: Pubescent. Color: 148B.

*Reproductive organs.*—Androecium: Present on disc florets only. Anther color: 14A. Pollen: Moderate, 14A in color. Gynoecium: Present on both ray and disc florets. Style color: 154C.

Disease resistance:

No known Chrysanthemum diseases observed to date on plants grown under commercial greenhouse conditions.

Seed production:

Seed production has not been observed.

CHART A

| CHARACTERISTIC | 'BLUE JAY' | 'DEBONAIR' |
|---|---|---|
| PLANT HEIGHT | About 22 cm | About 24 cm |
| LATERAL STEM LENGTH | About 20 cm | About 18.5 cm |
| STEM COLOR | 146C | 147C |
| LEAF LENGTH | About 5 cm | About 4.2 cm |
| LEAF WIDTH | About 4 cm | About 3.5 cm |
| PETIOLE LENGTH | About 2 cm | About 1.5 cm |
| YOUNG FOLIAGE, ADAXIAL | 137C | 147A |
| YOUNG FOLIAGE, ABAXIAL | 137D | 147B |
| QUANTITY OF INFLORESCENCES PER LATERAL STEM | 6 | 5 |
| BUD SHAPE | Flattened | Spherical |
| BUD COLOR | 70A | 65B |
| RAY FLORET COLOR WHEN OPENING, ADAXIAL | 70B | 82D |
| RAY FLORET COLOR, WHEN OPENING, ABAXIAL | 70D | 75D |
| RAY FLORET COLOR, MATURE, ADAXIAL | 77C | 84B |
| RAY FLORET COLOR, MATURE, ABAXIAL | 75C | 76D |
| RAY FLORET COLOR FADING TO | 75B | 84C |
| NUMBER OF RAY FLORETS PER INFLORESCENCE | About 156 | About 196 |
| NUMBER OF DISC FLORETS PER INFLORESCENCE | About 28 | About 8 |
| DISC FLORET COLOR, IMMATURE | 6A | 2B |
| DISC FLORET COLOR, MATURE | 6A | 2B |
| DIAMETER OF DISC | About 7 mm | About 3 mm |
| PEDUNCLE LENGTH, FIRST | About 3.8 cm | About 1.8 cm |
| PEDUNCLE LENGTH, FOURTH | About 6 cm | About 3.1 cm |
| PEDUNCLE STRENGTH | Strong | Moderately strong |
| PEDUNCLE ANGLE TO STEM | About 35° | About 30° |
| PEDUNCLE COLOR | 148B | 137D |

It is claimed:

1. A new and distinct cultivar of Chrysanthemum plant named 'Blue Jay', as illustrated and described.

* * * * *

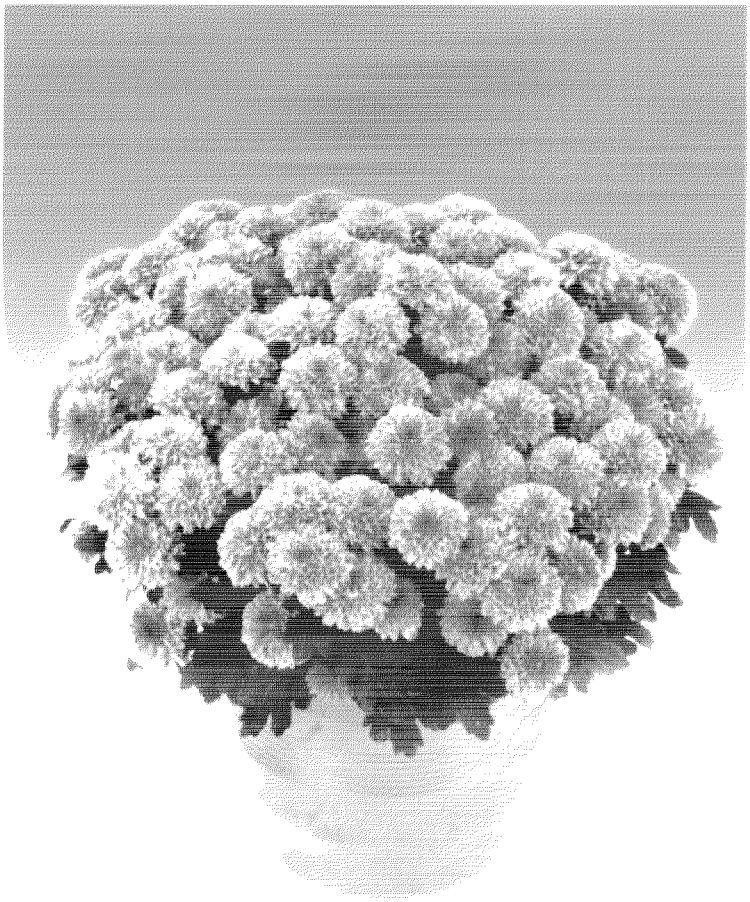

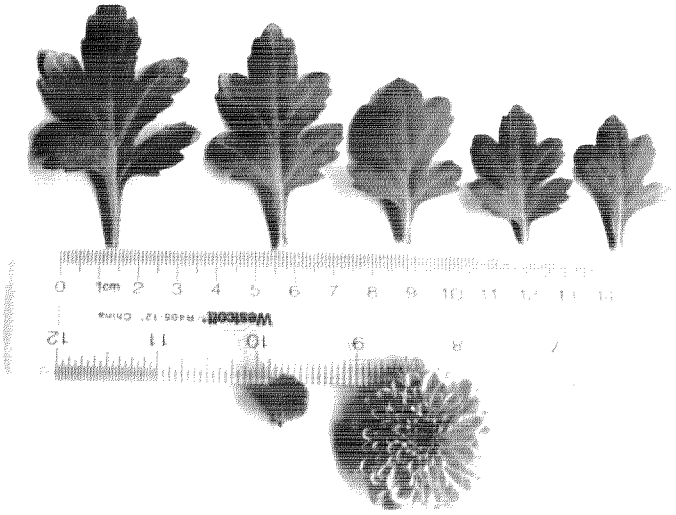
12 11 10 9 8 7
Westcott R406-12" China
0 1cm 2 3 4 5 6 7 8 9 10 11 12 13 14 15

UNITED STATES PATENT AND TRADEMARK OFFICE

CERTIFICATE OF CORRECTION

PATENT NO. : Plant 10,212
DATED : January 27, 1998
INVENTOR(S) : Peter Wain

It is certified that error appears in the above-indentified patent and that said Letters Patent is hereby corrected as shown below:

Column 3, line 49, replace

"*Quantity of inflorescences.*

—About 6 inflorescences per flowering stem. Diameter: About 4.3 cm. Depth (height): About 1.8 cm. Diameter of disc: About 7 mm." with -- *Quantity of inflorescences.*

—About 6 inflorescences per flowering stem.

*Inflorescence size:*

Diameter: About 4.3 cm. Depth (height): About 1.8 cm. Diameter of disc: About 7 mm. --.

Signed and Sealed this

Tenth Day of August, 1999

*Attest:*

Q. TODD DICKINSON

*Attesting Officer*

*Acting Commissioner of Patents and Trademarks*